US00PP37339P2

(12) United States Plant Patent
Hansen

(10) Patent No.: US PP37,339 P2
(45) Date of Patent: Mar. 24, 2026

(54) ***PANICUM* PLANT NAMED 'October Sky'**

(50) Latin Name: ***Panicum virgatum* (L.)**
Varietal Denomination: October Sky

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,830

(22) Filed: Sep. 23, 2025

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

(56) References Cited

U.S. PATENT DOCUMENTS

PP34,509 P2 * 8/2022 Hansen ..... Plt./384

* cited by examiner

*Primary Examiner* — Karen M Redden

(57) ABSTRACT

A new and distinct plant of ornamental Switch Grass named *Panicum* 'October Sky' with blue-green, upright and arching foliage that red-purple tips and blush in early September. The upright and dense culms produce medium-height plants with airy panicles beginning greyed-green and becoming reddish-purple in September before drying in the fall to tan seed heads that are retained into winter. The new plant is useful in the landscape as a specimen, en masse, or in a container.

2 Drawing Sheets

Latin botanical classification: *Panicum virgatum* (L.).
Variety denomination: 'October Sky'.

STATEMENT REGARDING PRIOR DISCLOSURES UNDER 37 CFR 1.77(B)(6)

The first offer for sale anywhere in the world was to Chad Walters by Walters Gardens, Inc. on Sep. 23, 2024. Walters Gardens, Inc. obtained the plant and all information relating thereto from the inventor. No plants of *Panicum* 'October Sky' have been sold or disclosed in this country or anywhere in the world more than one year prior to the filing date of this application, and any sale or disclosure within one year was either derived directly or indirectly from the inventor.

BACKGROUND OF THE PLANT

*Panicum* 'October Sky', hereinafter also referred to just by the cultivar name 'October Sky' and the "new plant" is a new and distinct cultivar of Switch Grass.

The new plant originated from a cross of 'Apache Rose' U.S. Plant Pat. No. 29,142 as the female parent and 'Northwind' (not patented) as the male parent at a wholesale perennial nursery in Zeeland, Michigan in the late summer of 2014. The seed was collected in the autumn of 2014 and sown the following spring. The individual seedling was initially selected from among many for further observation in the summer and fall of 2016 at which time it was assigned the breeder code 14-5-9 before giving the new plant a cultivar name.

The new plant has been successfully asexually propagated by division since late fall of 2018 at the same wholesale perennial plant nursery in Zeeland, MI, and found to produce stable and identical plants that maintain the unique characteristics of the original plant. The plant is stable and reproduces true-to-type in successive generations of asexual reproduction.

BRIEF SUMMARY OF THE PLANT

*Panicum* 'October Sky' differs from the female parent, 'Apache Rose', in that the new plant is taller, with tighter denser habit, and the foliage is more bluish and more cascading toward the leaf tips. 'Northwind' has a larger taller habit and has foliage with more green coloration and without purplish-red tinting.

The nearest comparison varieties known to the inventor are: 'Cape Breeze' U.S. Plant Pat. No. 24,895, 'Cheyenne Sky' U.S. Plant Pat. No. 23,209, 'Prairie Fire' U.S. Plant Pat. No. 19,367, 'RR1' U.S. Plant Pat. No. 17,944, and 'Shenandoah' (not patented).

'Cape Breeze' has significantly shorter and more compact and the foliage is not as blue-green in the summer. 'Cheyenne Sky' has a significantly shorter habit and more upright foliage that becomes concord purple earlier in the summer. 'Prairie Fire' is significantly shorter with more upright leaves and the foliage develops a deep wine color. 'RR1' has a shorter habit and the leaves color up earlier in the season to a purple-red. 'Shenandoah' has a shorter and more arching in habit, the culms are looser and not as densely arranged, and the foliage develops a red-purple color earlier in the season.

Table 1 below includes comparisons of other *Panicum* cultivars known to the inventor:

TABLE 1

| CULTIVAR | U.S. PLANT PAT. NO. | TOTAL HEIGHT (cm) | INITIAL COLOR |
|---|---|---|---|
| 'Apache Rose' | PP29,142 | 95 | gray-green |
| 'Cape Breeze' | PP24,895 | 75 | dark green |
| 'Cheyenne Sky' | PP23,209 | 112 | blue-green |
| 'Gunsmoke' | PP32,373 | 135 | blue-green |
| 'Haense Herms' | (not patented) | 100 | green |
| 'Hot Rod' | PP26,074 | 90 | blue-green |
| 'Northwind' | (not patented) | 180 | blue-green |
| 'October Sky' | current appl. | 170 | blue-green |
| 'Prairie Fire' | PP19,367 | 100 | blue-green |
| 'Red Flame' | PP35,213 | 120 | blue-green |
| 'Rostrahlbush' | (not patented) | 110 | green |
| 'RR1' | PP17,944 | 120 | blue-green |
| 'Shenandoah' | (not patented) | 140 | blue-green |

| CULTIVAR | SEASONAL COLOR | SEASON OF CHANGE BEGINNING | HABIT |
|---|---|---|---|
| 'Apache Rose' | purple-tipped | late July | dense upright |
| 'Cape Breeze' | purple-tipped | late September | compact upright |
| 'Cheyenne Sky' | concord purple | early July | very upright |
| 'Gunsmoke' | blue-green | none | upright arching |
| 'Haense Herms' | red-purple | early August | upright |
| 'Hot Rod' | red-purple | early spring | upright |
| 'Northwind' | yellow-green | September | upright |
| 'October Sky' | red-purple | early September | upright |
| 'Prairie Fire' | deep wine | early July | upright |
| 'Red Flame' | wine red | September | upright arching |
| 'Rostrahlbush' | red-purple | early August | upright |
| 'RR1' | purple-red | early July | compact |
| 'Shenandoah' | red-purple | late July | arching |

The following traits of *Panicum* 'October Sky' in combination have been repeatedly observed in multiple generations of asexually propagated plants and distinguish the new plant from all other Switch Grass plants known to the inventor:

1. Broad blue-green foliage develops red-purple tips and blush in early September;
2. Upright and dense culms producing medium height plants that do not lodge;
3. Foliage is upright and arching distally becoming tan in fall;
4. Panicles are upright and narrow with seed heads starting greyed-green and becoming reddish-purple in September and converting to tan seed heads that are retained into winter.

BRIEF DESCRIPTION OF THE DRAWINGS

The photographs of the new plant demonstrate the overall appearance of a six-year-old plant growing in an outdoor display garden in Zeeland, MI, including the unique traits. The colors are as accurate as reasonably possible with color reproductions. Ambient light spectrum, source, and direction may cause the appearance of minor variation in color.

DETAILED BOTANICAL DESCRIPTION

Figure 1:
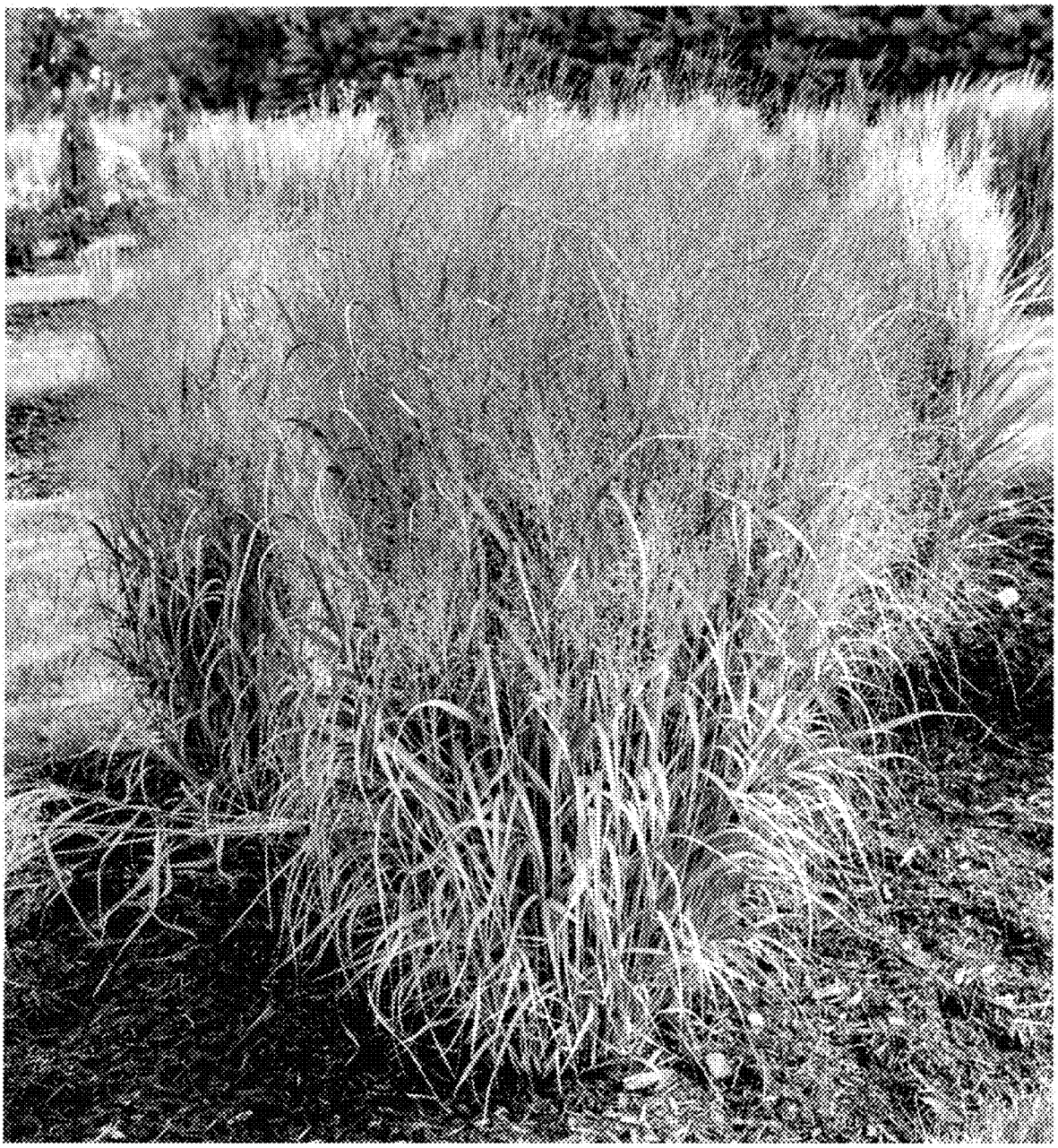
FIG. 1 shows the new plant with reddish-purple foliage in mid-September.
Figure 2:
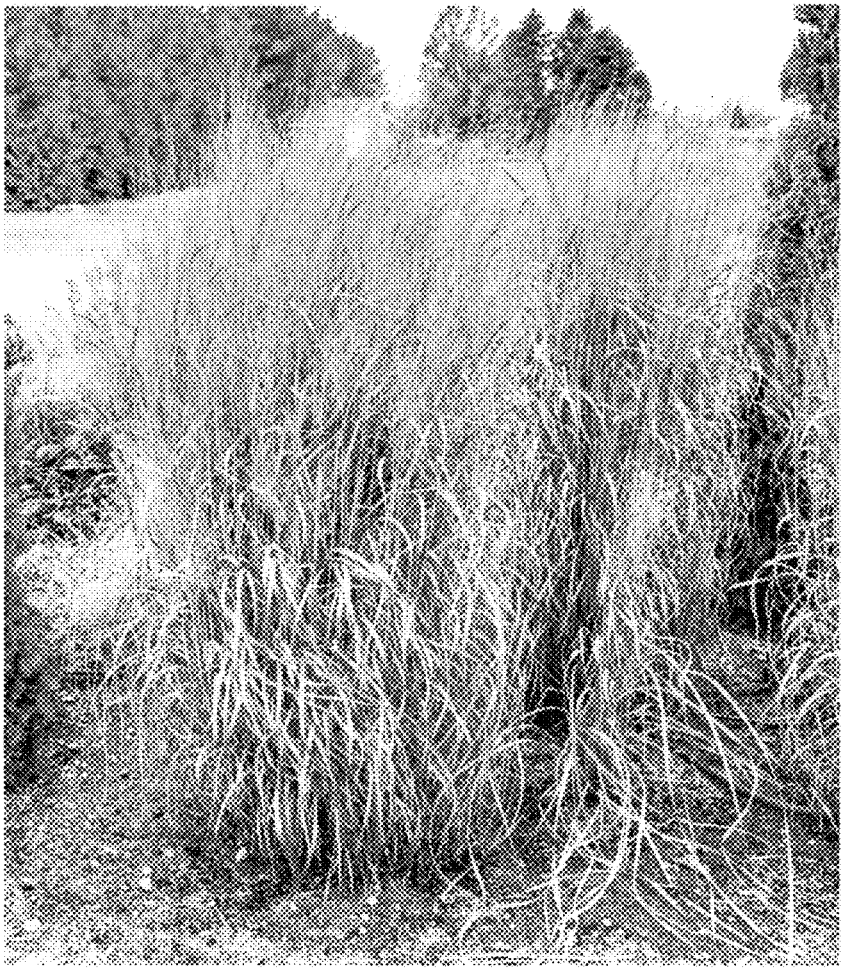
FIG. 2 shows the new plant in late October.
Figure 3:
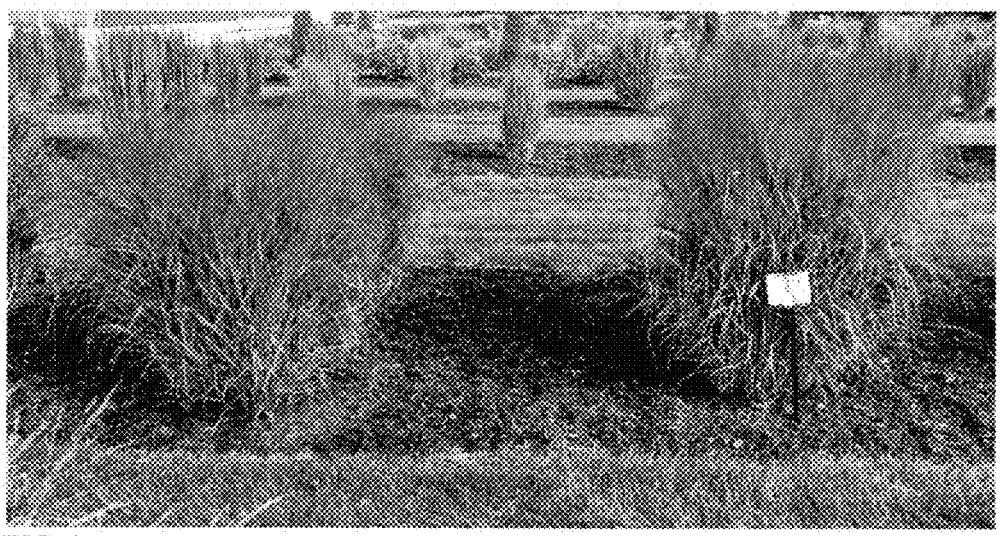
FIG. 3 shows a comparison of 'Apache Rose' on left and 'October Sky' on right.

The following descriptions and color references are based on the 2015 edition of The Royal Horticultural Society Colour Chart except where common dictionary terms are used. The new plant, 'October Sky', has not been observed in all possible environments. The phenotype may vary slightly with different environmental conditions, such as temperature, light, fertility, moisture, and maturity levels, but without any change in the genotype. The following observations and descriptions are of a six-year-old plant in a loamy-sand trial garden of a wholesale perennial nursery in Zeeland, Michigan, USA, grown in full sun with supplemental water and fertilizer as needed.

Parentage: Female (seed parent) 'Apache Rose', the male (pollen) parent is 'Northwind';

Propagation method: By division of the culms;

Time to finishing in a 3.8-liter pot: Moderately vigorous; about 10 to 12 weeks to finish from 25 mm diameter plug;

Rooting habit: Normal, coarsely branching; root color nearest RHS 155D;

Plant description:

Plant shape and habit: Hardy herbaceous perennial forming tightly, rhizomatous and upright culms with arching foliage, topped with finely-textured airy inflorescence producing a upright clump that is taller than it is wide;

Plant size: Foliage height at flowering time is about 165 cm tall from the soil line to the top of the foliage arch and 170 cm tall to the top of flowers; about 65 cm wide at the soil line and about 141 cm at the widest point about 62 cm above the soil;

Foliage description: Glabrous, glaucous; linear; flat; margin with micro-dentations; sheathed about two-thirds of the distance from the node of attachment of sheath, adaxial and abaxial surfaces dull; moderately arching; deciduous but persist through winter;

Foliage size: Blade to about 52 cm long and to about 13 mm wide; sheath and about 13 cm long; average blade about 46 cm long, average sheath about 11.5 cm long and 4 mm across; shorter at the proximal end; typically 6 leaves per culm;

Foliage color: Early and midseason adaxial between RHS N137D and RHS 189A, abaxial between RHS N137D and RHS 189A; September color developing adaxial leaf apices with between RHS N186D and RHS 186C and a faint blush toward leaf center, abaxial nearest RHS N137D with a faint blush distally of nearest RHS N186C; winter adaxial nearest RHS 164D, winter abaxial surface between RHS 165D and RHS 164D;

Veins: Parallel; midrib about 0.5 mm across; adaxial slightly recessed; abaxial costate; glabrous adaxial and abaxial;

Vein color: Adaxial midrib in proximal 5 to 7 cm nearest RHS 189A, adaxial distal midrib portion, secondary veins and abaxial midribs and secondary veins indistinguishable and same color as surrounding leaf;

Culm: Erect; terete, hollow; glabrous; glaucous; dull surface; about 70% enclosed by leaf sheath; about 125 culms per clump;

Culm dimension: To about 123 cm long without panicle, average about 108 cm; to about 4 mm diameter at base; internode length average about 17.8 cm, shorter proximally;

Culm color: Variable; where exposed between RHS 137B and RHS 189B; beneath sheath nearest RHS 145C;

Node description: About 6 per culm, slightly swollen to about 5 mm diameter;

Node color: Variable; proximally nearest RHS 200A, middle nearest RHS 160C, distally nearest RHS 147B;

Flower description: Finely-branched, narrow, airy panicle; one panicle per culm;

Flower timing: Beginning mid to late August, panicles dry and remain effective through winter;

No flower fragrance detected;

Panicle: Ellipsoidal with acute apex; to about 42 cm long and 18 cm wide near middle; overall effective color variable, beginning nearest RHS 145D, developing to both RHS N186C and RHS 187C, and maturing to between RHS NN155A and RHS 156D;

Rachis: Terete with irregular longitudinal ridges, compound branched; glabrous; glaucous; to about 36 cm long and about 3 mm diameter at base; branches to about 17 cm long and about 1 mm diameter held at about 50-degree angle above horizontal; color nearest RHS N138B;

Spikelet: Usually with two florets; about 14 mm long;

Rachilla: Thin, terete, stiff; to about 10 mm long and about 0.2 mm diameter; color nearest and RHS 187A;

Lower glume: Elliptical; about 2 mm long and 1 mm wide; without awn; color nearest RHS 186B;

Upper glume: Subulate to elliptical; about 4 mm long and 1 mm wide; without awn; color nearest RHS 186B distally and nearest;

Lemma: Without bristle; elliptical; acute apex, truncate base; margin entire; upper and lower each about 2 mm long and 0.7 mm wide; color nearest RHS 148C in middle, and nearest RHS 155D proximally;

Palea: Acute apex, truncate base, margin entire; about 2 mm long and 0.5 mm across; translucent, nearest RHS 155D;

Gynoecium: Two;

*Stigma*.—Two lobes, plumose, protruding about 1.5 mm from glume and about 0.5 mm diameter; color nearest RHS 187A.

*Style*.—Thin; about 1 mm long and 0.1 mm diameter; color transparent to nearest RHS 187A.

*Ovary*.—Ellipsoidal; acute apex, rounded base; about 1 mm long and 0.5 mm diameter; color between RHS 155D and RHS 148B;

Androecium: Typically, three;

*Filaments*.—Short; hair-like; up to 2 mm long and less than 0.1 mm diameter; color nearest RHS NN155D.

*Anthers*.—Two; dorsifixed, longitudinal; about 2 mm long and about 1 mm wide; color nearest RHS 187A prior to pollen dehiscing.

*Pollen*.—Abundant; less than 0.1 mm in diameter; color lighter than RHS N163A.

Fruit: Caryopsis; about 2.5 mm long and about 1 mm wide; color between RHS 161D and RHS 199D;

Hardiness: At least from USDA zone 4 through 9;

Growth: The new plant is very drought once established and the stems are resistant to lodging;

Disease and pest resistance or susceptibility: 'October Sky' has superior rust (*Puccinia* sp.) resistance compared to 'Northwinds'. Other disease resistance or susceptibility beyond that. typical of other Switch Grasses has not been observed.

I claim:

1. A new and distinct cultivar of *Panicum* plant named 'October Sky' as herein described and illustrated.

* * * * *